United States Patent [19]

Ottenheijm

[11] Patent Number: 4,820,712
[45] Date of Patent: Apr. 11, 1989

[54] SPARSOMYCIN (SC-RS) COMPOUNDS HAVING ANTITUMOR ACTIVITY, A PROCESS FOR THEIR PREPARATION AND PHARMACEUTICAL COMPOSITIONS CONTAINING SPARSOMYCIN (SC-RS) COMPOUNDS

[75] Inventor: Henricus C. J. Ottenheijm, Milsbeek, Netherlands

[73] Assignee: Stichting Katholieke Universiteit, Netherlands

[21] Appl. No.: 900,779

[22] Filed: Aug. 27, 1986

[51] Int. Cl.$^4$ .................. A61K 31/505; C07D 239/54
[52] U.S. Cl. .................................. 514/274; 514/212; 540/607; 544/310; 544/311
[58] Field of Search .................. 544/311, 314, 310; 514/274, 212; 540/607

[56] References Cited
U.S. PATENT DOCUMENTS
4,581,360  4/1986  Ottenheijm et al. .................. 544/311

OTHER PUBLICATIONS
Helquist et al, Journal of the American Chemical Society (1979), vol. 101, pp. 1057-1059.
Koziol, Chemical Abstract 66-54328u (1967).

Primary Examiner—Donald G. Daus
Assistant Examiner—Cecilia Shen
Attorney, Agent, or Firm—Scully, Scott, Murphy & Presser

[57] ABSTRACT

The invention relates to novel sparsomycin ($S_c$-$R_s$) compounds having valuable antitumor activity, and to a process for their preparation and pharmaceutical compositions containing such novel compounds. The novel compounds satisfy the general formula

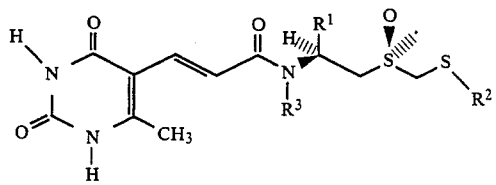

10 Claims, No Drawings

SPARSOMYCIN (SC-RS) COMPOUNDS HAVING ANTITUMOR ACTIVITY, A PROCESS FOR THEIR PREPARATION AND PHARMACEUTICAL COMPOSITIONS CONTAINING SPARSOMYCIN (SC-RS) COMPOUNDS

The invention relates to novel sparsomycin ($S_c$-$R_s$) compounds having valuable pharmaceological properties, in particular a strong antitumor acitivity, a relatively low toxicity, a good solubility in aqueous media and a potentiating effect on the cytostatic activity of other cytostatics, such as, for example, cis-platinum and 5-fluorouracil.

The invention also relates to pharmaceutical compositions containing such novel sparsomycin ($S_c$-$R_s$) compounds, and to a process for preparing said novel sparsomycin ($S_c$-$R_s$) compounds.

Sparsomycin is a metabolite of *Sterptomyces sparsogenes* (Antimicrob. Agents Chemother. (1962), 780) and of *Streptomyces cuspidosporus* (Chem. Abstr. (1967), 66, 543289) and has the structure formula:

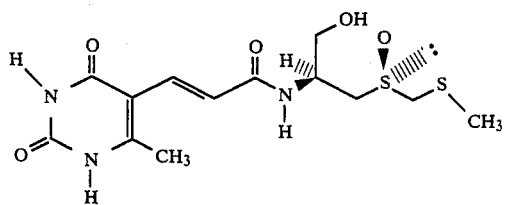

Sparsomycin has attracted much attention on account of its interesting biological activity. This activity is primarily a result of a strong inhibition of the protein biosynthesis resulting in a decline of the protein synthesis and concomitant biological effects. It has been shown (Ann. Rev. Microb. (1971), 25, 488; FEBS Lett. (1974), 40, 1 S63; Molec. Biol. Biochem. Biophys. (1979), 30) that the site of interaction of sparsomycin is in the large ribosomal subunit, where it prevents peptide transfer by interfering with the peptidyl transferase centre. The action of sparsomycin has been demonstrated in prokaryotic cells (L. Slechta: "Antibiotics I", Editors: D. Gottlieb and P. S. Shaw, Springer Verlag, New York (1967), 410; Can. J. Microb. (1967), 62, 595), eukaryotic cells (Biochem. Biophys. Res. Comm. (1966), 23, 453; J. Antibiot. (1978), 31, 598; Biochem, (1977), 16, 3209), including transformed cells (J. Med. Chem. (1977), 20, 337; antimicrob. Ag. Chemother. (1962), 772; Biochim. Biphys. Acta (1979), 563, 479; Cancer Res. (1972), 32, 398) and virus-infected cells (J. Virol. (1979), 29, 114; J. Gen. Virol. (1968), 2, 143), and in various cell-free systems (Biochem. Biophys. Acta (1966), 129, 642; Biochim. Biophys. Acta (1976), 447, 460; Proc. Natl. Acad. Sci. U.S.A. (1968), 61, 726; FEBS Lett. (1975), 52, 236). On the other hand, sparsomycin is not active against whole reticulocytes (Biochim. Biophys. Acta (1966), 119, 109), which is attributed to sparsomycin's being unable to penetrate these cells. The behaviour of sparsomycin with regard to its inhibitory action and its influence on the polyribosomes has also been investigated in vivo (Proc. Natl. Acad. Sci. U.S.A. (1968), 59, 854, J. Natl. Canc. Inst. (1979), 63, 81; Biochem. Pharmacol. (1974), 23, 857).

In connection with the demonstrated activity of sparsomycin against transformed cells and various tumors (Antimicrob. Agents Chemother. (1962), 772), it has been investigated as a potential cytostatic compound, but clinical tests (Cancer. Chemother. Rep. (1969), 43, 29) revealed eye toxicity.

In order to gain an insight into the biochemical interaction mechanism and the relationship between structure and activity, various researchers have prepared derivatives of sparsomycin and investigated their activity. In the absence of a total synthesis, however, only a limited number of derivatives could be investigated, which each differed from sparsomycin itself in various structural parameters. As a result, only limited conclusions could be drawn as to the role of the various structural fragments. Another problem in the interpretation and comparison of the available information as to the relationship between structure and activity in sparsomycin is that the biological activity of the various derivatives has been determined in different systems: in vitro in a KB cell culture (J. Med. Chem. (1977), 20, 337) or in cell-free ribosmal systems (Biochem. Biophys. Res. Comm. (1977), 75, 563; J. Med. Chem. (1978), 21, 177), in vivo in the P-388 system and the Walker 256 system (J. Pharm. Sci. (1975), 64, 825).

Recently a few total synthesis for sparsomycin and derivatives thereof have become available (J. Am. Chem. Soc. (1979), 101, 1057; J. Org. Chem. (1981), 46, 3273; J. Org. Chem. (1981), 46, 5408). These total snythesis enabled the present inventors to carry out an investigation in which various suitably selected derivatives of sparsomycin were prepared and their cytostatic activity was investigated in an in vitro clonogenic L 1210 assay, whereby the inhibition of colony formation was measured.

Said prior investigation, which forms the basis of Dutch patent application No. 8204224 (U.S. Pat. No. 4,581,360) concerned sparsomycin ($S_c$-$R_s$) derivatives in which the S-bound terminal methyl group was replaced by a more lipophilic group, preferably a $C_1$-$C_{20}$ alkyl group, aryl group, aralkyl group or alkaryl group. Exemplified representatives of said lipophilic group are n-octyl and benzyl. The n-octylsparsomycin is poorly dissolved in water (about 0.2 mg/ml water) whereas benzylsparsomycin dissolves much better in water (1.5 mg/ml water).

The investigation concerned further comprised sparsomycin ($S_c$-$R_s$) derivatives in which the hydroxymethyl group was etherified or esterified.

The compounds concerned were prepared by a process which started from D-cysteine or D-cystine.

It has now been found that novel sparsomycin ($S_c$-$R_s$) compounds can be obtained from much cheaper L-amino acids as starting material, said novel compounds being characterized by a different group at the location of the hydroxymethyl group and having valuable pharmacological properties.

In a first aspect, the present invention provides a sparsomycin ($S_c$-$R_s$) compound having the general formula

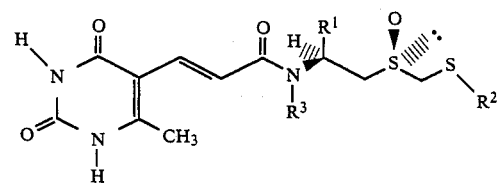

wherein:

$R^1$ represents $C_1-C_6$ alkyl or substituted $C_1-C_6$ alkyl, with the exception of hydroxymethyl, alkoxymethyl and acyloxymethyl;
phenyl or substituted phenyl;
heterocyclyl or substituted heterocyclyl;
benzyl or substituted benzyl;
heterocyclylmethyl or substituted heterocyclylmethyl;
$C_3-C_7$ cycloalkyl or substituted $C_3-C_7$ cycloalkyl;
$C_3-C_7$ cycloalkylmethyl or subsituted $C_3-C_7$ cycloalkylmethyl;
$R_2$ represents $C_1-C_{10}$ alkyl or substituted $C_1-C_{10}$ alkyl;
phenyl or substituted phenyl;
heterocyclyl or substituted heterocyclyl;
benzyl or substituted benzyl;
heterocyclylmethyl or substituted heterocyclylmethyl;
$C_3-C_7$ cycloalkyl or substituted $C_3-C_7$ cycloalkyl;
$C_3-C_7$ cycloalkylmethy or substituted $C_3-C_7$ cycloalkylmethyl;
$R_3$ represents hydrogen;
or $R^3$ and $R^1$, combined with the nitrogen atom and carbon atom to which they are respectively attached, form a three to seven membered, substituted or unsubstituted heterocyclic ring which may contain up to 3 additional heteroatoms in the ring selected from the group consisting of N, O and S; and pharmaceutically acceptable salts thereof.

In a preferred embodiment of the invention, $R^1$ represents
$C_1-C_4$ alkyl, optionally substituted by one or more substitents selected from the group consisting of $SO_3H$, $COOH$, $CONH_2$, $CONHR^4$, $CONR^4R^5$, $NH_2$, $NHR^4$, $NR^4R^5$, $NH-C(NH_2)=NH$, $NHCOR^4$, $N_3$, $NO_2$, and halogen;
phenyl or benzyl, optionally substituted by one or more substituents selected from the group consisting of OH, SH, $SO_3H$, COOH, $C_1-C_4$ alkyl, $C_1-C_4$ alkoxy, $C_1-C_4$ alkylthio, $C_1-C_4$ acyl, $C_1-C_4$ acyloxy, $C_1-C_4$ acylamido, $N_3$, $NO_2$, $NH_2$, $NHR^4$, $NR^4R^5$, and halogen;
imidazolemethyl or 3-indolylmethyl;
$R^2$ represents $C_1-C_6$ alkyl, optionally substituted by one or more substituents selected from the group consisting of OH, SH, $SO_3H$, COOH, $CONH_2$, $CONHR^4$, $CONR^4R^5$, $NH_2$, $NHR^4$, $NR^4R^5$, $NHCOR^4$, $N_3$, $NO_2$, and halogen, phenyl or benzyl, optionally substituted by one or more substituents selected from the group consisting of OH, SH, $SO_3H$, COOH, $C_1-C_4$ alkyl, $C_1-C_4$ alkoxy, $C_1-C_4$ alkylthio,
$C_1-C_4$ acyl, $C_1-C_4$ acyloxy, $C_1-C_4$ acylamido, $N_3$, $NO_2$, $NH_2$, $NHR^4$, $NR^4R^5$, and halogen;
$R^3$ represents hydrogen;
or $R^3$ and $R^1$, taken together, represents $-(CH_2)_3-$;
$R^4$ represents $C_1-C_4$ alkyl, phenyl or benzyl;
$R^5$ represents $C_1-C_4$ alkyl; and pharmaceutically acceptable salts thereof.

Specific examples of novel sparsomycin ($S_c-R_s$) compounds according to the present invention include the compounds:
(2a): ala-sparsomycin ($R^1$=methyl; $R^2$=methyl; $R^3$=hydrogen; prepared from L-alanine as starting material);
(2b): val-sparsomycin ($R^1$=isopropyl; $R^2$=methyl; $R^3$=hydrogen; prepared from L-valine as starting material);
(2c): ile-sparsomycin ($R^1$=sec. butyl; $R^2$=methyl; $R^3$=hydrogen; prepared from L-isoleucine as starting material);
(2d): phe-sparsomycin ($R^1$=benzyl; $R^2$=methyl; $R^3$=hydrogen; prepared from L-phenylalanine as starting material);
(2e): n-butyl-ala-sparsomycin ($R^1$=methyl; $R^2$=n-butyl; $R^3$=hydrogen);
(2f): n-octyl-ala-sparsomycin ($R^1$=methyl; $R^2$=n-octyl; $R^3$=hydrogen);
(2g): pro-sparsomycin having the structural formula

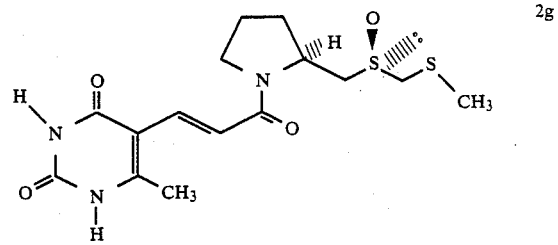

(prepared from L-proline as starting material).

Apart from the singificant economic advantage that the novel sparsomycin ($S_c-R_s$) compounds can be prepared from much cheaper L-aminoacids as starting material, they appear to combine a strong antitumor activity with a good solubility in aqueous systems and a relatively low toxicity.

As has been described earlier, the antitumor activity is correlated to the lipophilicity of the compound. There appears to be an optimum, however, since too high a lipophilicity may result in undesirably low solubility characteristics in aqueous systems.

Of the previously examined compounds, n-octylsparsomycin seems to be beyond such optimum in that it has such low water solubility to interfere with a proper determination of its $LD_{50}$ value.

The compounds of the present invention, such as, for example, ala-sparsomycin (2a) surprisingly appear to be closer to the optimum in that they combine a higher water solubility with a stronger antitumor activity and a relatively low toxicity.

The best combination of pharmacological properties is expected to be found with sparsomycin ($S_c-R_s$) compounds according to the present invention, in which $R^1$ contains one or more substituents that improve the water solubility, such as, for example, $SO_3H$ groups, and in which $R^2$ represents an alkyl group having about 2 or 3 to 4 or 5 carbon atoms or a benzyl group.

The present invention also provides pharmaceutical compositions comprising a pharmaceutically acceptable carrier, diluent, solvent or excipient and a therapeutically effective amount of a sparsomycin ($S_c-R_s$) compound according to the invention.

The compositions may also contain other active ingredients, such as other antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens of active ingredient for a given mammalian host can be readily ascertained by those skilled in the art. It will, of course, be appreciated that the actual dose used will vary according to the particular composition formulated, the mode of application and the particular situs, host and condition being treated. Many factors that modify the action of the drug will be taken into account including age, weight, sex, diet, time of administration, route of administration, rate of excretion, condition of the patient, drug combinations, reaction sensitivities and severity of the condition.

The novel compounds according to the invention appear very useful in combination therapies with known cytostatics such as cis-platinum and 5-fluorouracil which have wide-spread clinical use. Even very low nontoxic doses of the novel compounds result in a significant potentiation of the antitumor activity of said known cytostatics.

In another aspect, the present invention provides a process for preparing the novel sparsomycin ($S_c$—$R_s$) compounds comprising a series of reactions to convert an L-amino acid having the general formula

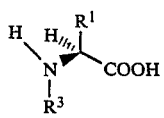

into a compound having the general formula

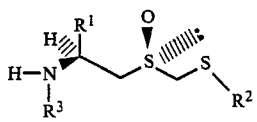

and reacting said compound (12) with 6-methyl-uracil acrylic acid having the structural formula

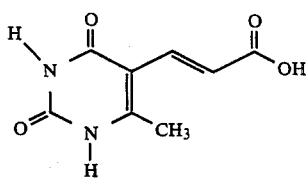

More specifically, in a preferred embodiment said process comprises the steps of reacting an L-aminoacid methyl ester with di-tert.butyl pyrocarbonate to obtain an N-(tert.butyloxycarbonyl)-L-aminoacid methyl ester having the general formula

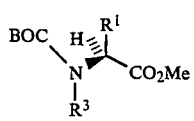

reacting said compound (4) with a reducing agent to obtain a compound having the general formula

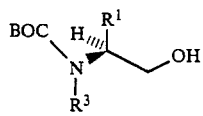

tosylating said compound (5) to obtain a compound having the general formula

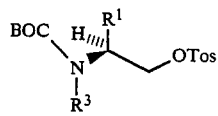

reacting said compound (6) with cesium carbonate and thioacetic acid to obtain a thioester having the general formula

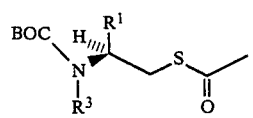

reacting said thioester (7) with acetic anhydride and chlorine to obtain the corresponding sulfinyl chloride, reacting said sulfinyl chloride with diazomethane to obtain the diasteromeric α-chloro sulfoxides

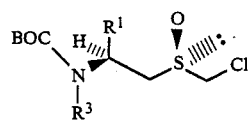

and

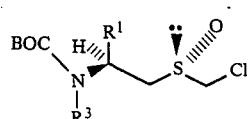

separating said diastereomers and isolating the ($S_c$—$R_s$) α-chloro sulfoxide (8), reacting same with a mercaptide having the general formula $MSR^2$ wherein M represents alkalimetal to obtain a compound having the general formula

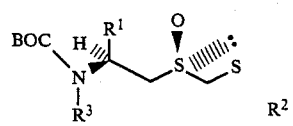

deprotecting the amino group by treatment with trifluoroacetic acid to obtain a compound having the general formula

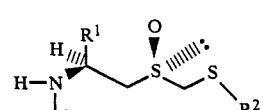

and reacting same with 6-methyl-uracil acrylic acid.

Said process is shown schematically in the following reaction scheme:

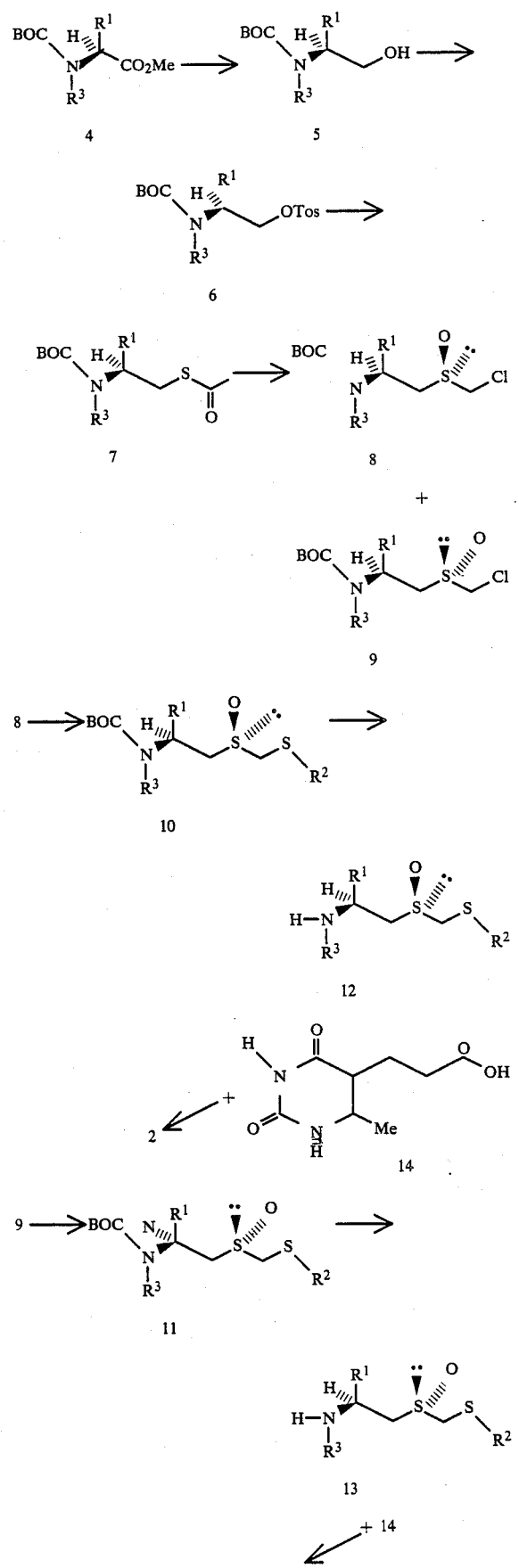

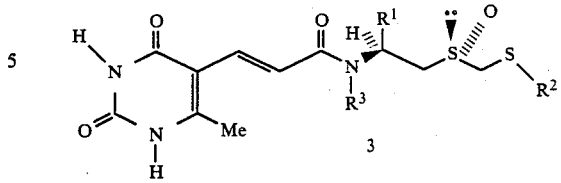

The pharmacological properties and preparation of sparsomycin ($S_c$—$R_s$) compounds according to the invention are shown in the following experimental part, which is provided for illustrative purposes only and should not be construed as limiting the scope of the invention.

EXPERIMENTAL SECTION

Melting points were determined in a Reichert hot stage and are uncorrected, $^1$H NMR spectra were recorded on a Bruker WH-90 spectrometer with Me$_4$Si or Me$_3$SiCD$_2$CD$_2$CO$_2$Na as an internal standard. Mass spectra were recorded on a double-focussing VG 7070E mass spectrometer. Circular dichroism (CD) spectra were recorded with an Auto-dichrograph Mark V apparatus (Jobin Yvon). For determination of the specific rotation, a Perkin-Elmer 241 polarimeter was used. Thin-layer chromatography (TLC) was carried out by using Merck precoated silicagel F-254 plates (thickness 0.25 mm). Spots were visualized with a UV lamp, ninhydrin and Cl$_2$-TDM. For column chromatography, Merck silicagel H (type 60) was used.

References

1. Ottenheijm et at. J. Org. Chem. 46, 3273–3283 (1981).
2. Liskamp et al, J. Med. Chem. 27, 301–306 (1984).

N-(tert.-butyloxycarbonyl)-L-alanine methyl ester (4a)

This compound was prepared in 93% yield from the hydrochloride of L-alanine methyl ester (13.2 g, 103.4 mmol) by treatment with di-tert.-butyl pyrocarbonate following the procedure that has been described earlier[1,2]. TLC $R_f$ 0.80 (eluent MeOH/CHCl$_3$, 3/97). $^1$H NMR (CDCl$_3$) δ 1.36 (d, J=5 Hz, 3H, CHCH$_3$), 1.50 (s, 9H, t-Bu), 3.76 (s, 3H, CO$_2$CH$_3$), 4.03–4.65 (m, 1H, CHCH$_3$), 5.50 (br d, 1H, NH).

N-(tert.-butyloxycarbonyl)-L-valine methyl ester (4b)

This compound was prepared in quantitative yield from the hydrochloride of L-valine methyl ester (25.2 g. 0.15 mol) by treatment with di-tert.-butyl pyrocarbonate following the procedure that has been described earlier[1,2]. TLC $R_f$ 0.85 (eluent MeOH/CHCl$_3$, 3/97). $^1$H NMR (CDCl$_3$) δ 0.87 and 0.98 (dd, J=2 Hz, 6H, CH$_3$CHCH$_3$), 1.45 (s, 9H, t-Bu), 1.77–2.37 (m, 1H, CH$_3$CHCH$_3$), 3.75 (s, 3H, CO$_2$CH$_3$), 4.01–4.37 (m, 1H, CHCO$_2$CH$_3$), 4.90–5.29 (m, 1H, NH).

N-(tert.-butyloxycarbonyl)-L-isoleucine methyl ester (4c)

This compound was prepared in 99% yield from the hydrochloride of L-isoleucine methyl ester (27.3 g, 0.15 mol) by treatment with di-tert.-butyl pyrocarbonate following the procedure that has been described earlier[1,2]. TLC $R_f$ 0.85 (eluent MeOH/CHCl$_3$, 3/97). $^1$H NMR (CDCl$_3$) δ 0.73–0.99 (m, 6H, CH$_2$CH$_3$, CHCH$_3$), 1.06–1.41 (m, 2H, CH$_2$CH$_3$), 1.44 (s, 9H, t-Bu), 3.27–3.67 (m, 1H, CHCH₃), 3.73 (s, 3H, CO₂CH₃), 4.03–4.40 (m, 1H, CHCO₂CH₃), 4.77–5.20 (m, 1H, NH).

N-(tert.-butyloxycarbonyl)-L-phenylalanine methyl ester (4d)

This compound was prepared in 97% yield from the hydrochloride of L-phenylalanine methyl ester (32.4 g, 0.15 mol) by treatment with di-tert.-butyl pyrocarbonate following the procedure that has been described earlier[1,2]. TLC R$_f$ 0.85 (eluent MeOH/CHCl₃, 3/97). ¹H NMR (CDCl₃) δ 1.40 (s, 9H, t-Bu), 3.04 and 3.11 (d, AB part of ABX spectrum, 2H, CHCH₂), 3.70 (s, 3H, CO₂CH₃), 4.36–4.73 (m, 1H, CHCO₂CH₃), 4.75–5.10 (m, 1H, NH), 7.04–7.34 (m, 5H, Ph).

N-(tert.-butyloxycarbonyl)-L-proline methyl ester (4g)

This compound was prepared in quantitative yield from the hydrochloride of L-proline methyl ester (24.9 g, 0.15 mol) by treatment with di-tert.-butyl pyrocarbonate following the procedure that has been described earlier[1,2]. TLC R$_f$ 0.83 (eluent MeOH,CHCl₃, 3/97). ¹H NMR (CDCl₃) δ 1.44 (s, 9H, t-Bu), 1.82–2.37 (m, 4H, CH₂CH₂CH), 3.33–3.65 (m, 2H, CH₂N), 3.73 (s, 3H, CO₂CH₃), 4.04–4.45 (m, 1H, CHCO₂CH₃).

N-(tert.-butyloxycarbonyl)-L-alaninol (5a)

This compound was prepared in 90% yield from the ester 4a (2.44 g, 12 mmol) by reduction with lithium borohydride in dry DME analogous to the method described earlier[1,2]. The product was used for the next reaction without further purification. ¹H NMR (CDCl₃) δ 1.14 (d, J=6.6 Hz, 3H, CHCH₃), 1.44 (s, 9H, t-Bu), 2.71 (br s, 1H, CH₂OH), 3.45 and 3.55 (AB part of ABX spectrum, 7 lines, J$_{AX}$=4.7 Hz, J$_{BX}$=7.4 Hz, J$_{AB}$=10.1 Hz, 2H, 2H, CH₂OH), 3.47–3.95 (m, 1H, CHCH₃), 4.68 (br d, 1H, NH). Anal. Calcd. for C₈H₁₇NO₃: C, 54.84; H, 9,78; N, 7.99. Found: C, 54.84; H, 9.96; N, 7.96.

N-(tert.-butyloxycarbonyl)-L-valinol (5b)

This compound was prepared in 81% yield from the ester 4b (9.28 g, 40 mmol) by reduction with lithium borohydride in dry DME following the procedure that has been described earlier[1,2]. TLC R$_f$ 0.47 (eluent MeOH/CHCl₃,7/93). ¹H NMR (CDCl₃) δ 0.91 and 0.98 (dd, J=2 Hz, 6H, CH₃CHCH₃), 1.44 (s, 9H, t-Bu), 1.45–1.97 (m, 1H, CH₃CHCH₃), 2.15 (s, 1H, OH), 3.24–3.49 (m, 1H, CHCH₂), 3.53–3.72 (m, 2H, CH₂OH), 4.36–4.77 (m, 1H, NH). CI MS, m/e 204 (M⁺+1).

N-(tert.-butyloxycarbonyl)-L-isoleucinol (5c)

This compound was prepared in 97% yield from the ester 4c (9.84 g, 40 mmol) by reduction with lithium borohydride in dry DME analogous to the method described earlier[1,2]. TLC R$_f$ 0.47 (eluent MeOH/CHCl₃, 7/93). ¹H NMR (CDCl₃) δ 0.83–1.03 (m, 6H, CHCH₃, CH₂CH₃), 1.03–1.40 (m, 2H, CH₂CH₃, CH₂CH₃), 1.44 (s, 9H, t-Bu), 2.21–2.61 (m, 1H, CHCH₃), 3.32–3.88 (m, 4H, CHCH₂OH), 4.52–4.68 (m, 1H, NH). CI MS, m/e 218 (M⁺+1).

N-(tert.-butyloxycarbonyl)-L-phenylalaninol (5d)

This compound was prepared in 89% yield from the ester 4d (11.2 g, 40 mmol) by reduction with lithium borohydride in dry DME analogous to the method described earlier[1,2]. TLC R$_f$ 0.50 (eluent MeOH/CHCl₃, 7/93). ¹H NMR (CDCl₃) δ 1.40 (s, 9H, t-Bu), 2.00–2.53 (m, 1H, OH), 2,83 (d, J=5.4 Hz, 2H, CH₂Ph), 3.33–4.08 (m, 3H, CH₂OH, CHCH₂), 4.48–4.94 (br d, 1H, NH), 7.22 (s, 5H, Ph). CI MS, m/e 252 (M⁺+1).

N-(tert.-butyloxycarbonyl)-L-prolinol (5g)

This compound was prepared in 92% yield from the ester 4g (9.2 g, 40 mmol) by reduction with lithium borohydride in dry DME following the procedure that has been described earlier[1,2]. TLC R$_f$ 0.81 (eluent MeOH/CHCl₃, 7/93). ¹H NMR (CDCl₃) δ 1.47 (s, 9H, t-Bu), 1.58–2.18 (m, 4H, CH₂CH₂CH), 3.15–3.66 (m, 4H, CH₂N, CH₂OH), 3.73–4.07 (m, 1H, CHN), 4.40–4.80 (br s, 1H, OH).

(S)-1-hydroxy-O-(p-toluenesulfonyl)-2-amino-N-(tert.-butyloxycarbonyl)-propane (6a)

To a solution of the alcohol 5a (11.4 mmol) in 75 mL of dry pyridine was added tosyl chloride (12.5 mmol) at −10° C. The reaction mixture was stirred at 4° C. overnight. After completion of the reaction as was monitored by TLC (eluent MeOH/CHCl₃, 5/95), most of the pyridine was removed by evaporation in vacuo at room temperature. The residue wad dissolved in 200 mL of dichloromethane and subsequently washed two times with a 2N KHSO₄ solution to remove pyridine and then with water. The organic layer was dried (Na₂SO₄) and the solvent was evaporated in vacuo at room temperature. The crude product was obtained as a white solid in 87% yield. The crystalline product was not purified by recrystallization because of the instability of this compound. Even at room temperature, in attempts to recrystallize the product, it decomposes into the cyclic urethane

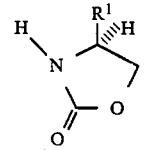

For 6a: TLC R$_f$ 0.79 (eluent MeOH/CHCl₃, 5/95). ¹H NMR (CDCl₃) δ 1.15 (d, J=6.5 Hz, 3H, CHCH₃), 1.37 (s, 9H, t-Bu), 2.44 (s, 3H, Ph-CH₃), 3.67–4.11 (m, 1H, CHCH₃), 3.95 (br s, 2H, CH₂OH), 4.53 (br d, 1H, NH), 7.22 and 7.73 (ABq, J$_{AB}$=8 Hz, 4H, Ph-H), CI MS, m/e 300 (M⁺+1).

(S)-1-hydroxy-O-(p-toluenesulfonyl)-2-amino-N-(tert.butyloxycarbonyl)-3-methyl-butane (6b)

This compound was prepared in 70% yield from compound 5b (3.0 g, 14.8 mmol) as described for the synthesis of compound 6a. TLC R$_f$ 0.29 (eluent diisopropyl ether/hexane, 1/1). ¹H NMR (CDCl₃) δ 0.82–0.98 (m, 6H, CH₃CHCH₃), 1.40 (s, 9H, t-Bu), 1.49–1.92 (m, 1H, CH₃CHCH₃), 2.44 (s, 3H, pH-CH₃), 3.30–3.73 (m, 1H, CHCH₂), 3.86–4.22 (AB part of ABX spectrum, 2H, CHCH₂), 4.31–4.73 (m, 1H, NH), 7.34 and 7.76 (ABq, J$_{AB}$=9 Hz, 4H, Ph-H).

(S)-1-hydroxy-O-(p-toluenesulfonyl)-2-amino-N-(tert.-butyloxycarbonyl)-3-methyl-pentane (6c)

Following the same procedure as used for the preparation of compound 6a, this compound was prepared in 85% yield from compound 5c (5.0 g, 23 mmol). TLC R$_f$ 0.27 (eluent diisopropyl ether/hexane, 1/1). ¹H NMR (CDCl₃) δ 0.70–1.00 (m, 6H, CH₃CHCH₃), 1.03–1.89

(m, 3H, CHCH₂CH₃), 1.40 (s, 9H, t-Bu), 2.44 (s, 3H, Ph-CH₃), 3.30–3.80 (m, 1H, CHCH₂O), 4.03 and 4.07 (AB part of ABX spectrum, d, 2H, CHCH₂O), 4.59 (br d, J=4.5 Hz, 1H, NH), 7.33 and 7.77 (ABq, J=8.1 Hz, 4H, Ph-H).

(S)-1-hydroxy-O-(p-toluenesulfonyl)-2-amino-N-(tert.-butyloxycarbonyl)-3-phenyl-propane (6d)

Following the same procedure as used for the preparation of compound 6a, this compound was prepared in 89% yield from compound 5d (5.78 g, 23 mmol). TLC $R_f$ 0.23 (eluent diisopropyl ether/hexane, 1/1). ¹H NMR (CDCl₃) δ 1.37 (s, 9H, t-Bu), 2.43 (s, 3H, Ph-CH₃), 2.68–3.00 (AB part of ABX spectrum, m, 2H, CHCH₂Ph), 3.83–4.22 (m, 3H, CHCH₂O), 4.56–4.86 (m, 1H, NH), 6.98–7.23 (m, 5H, CH₂Ph-H), 7.32 and 7.74 (ABq, $J_{AB}$=9 Hz, 4H, Ph-H).

Tosylate of N-(tert.-butyloxycarbonyl)-L-prolinol (6g)

This compound was prepared in 99% yield from compound 5 g (6.0 g, 30 mmol) as described for the synthesis of compound 6a. TLC $R_f$ 0.81 (eluent MeOH/CHCl₃, 4/96). ¹H NMR (CDCl₃) δ 1.39 (s, 9H, t-Bu), 1.63–2.12 (m, 4H, CH₂CH₂CH), 2.44 (s, 3H, Ph-CH₃), 3.11–3.54 (AB part of ABX spectrum, m, 2H, CHCH₂O), 3.76–4.26 (m, 3H, CH₂N, CHCH₂O), 7.37 and 7.79 (ABq, $J_{AB}$=8 Hz, 4H, Ph-H).

(S)-1-thio-S-acetyl-2-amino-N-(tert.-butyloxycarbonyl)propane (7a)

To a suspension of cesium carbonate (18.5 g, 57 mmol) in 60 mL of dry DMF was added freshly distilled thioacetic acid (9.0 g, 119 mmol). Previously, nitrogen had been passed through the suspension for 15 min. When the cesium carbonate was dissolved, the crude tosylate 6a (28.8 g, 96 mmol) dissolved in 40 mL of dry DMF was added. The reaction mixture was stirred in the dark for 16 hrs at room temperature and was kept under a nitrogen atmosphere. The reaction was monitored by TLC (eluent diisopropyl ether/hexane, 1/1). After completion of the reaction the solvent was evaporated in vacuo. The residue was dissolved in 300 mL of dichloromethane and subsequently washed two times with 200 mL 0.5N NaOH solution and once with water. The organic layer was dried (Na₂SO₄) and concentrated in vacuo. The crude reaction product was subjected to column chromatography (silicagel, eluent diisopropyl ether/hexane, 1/1) to give 7a in 80% yield. The yield is based on the alcohol 5a. TLC $R_f$ 0.37 (eluent diisopropyl ether/hexane, 1/1). ¹H NMR (CDCl₃) δ 1.15 (d, J=6.5 Hz, 3H, CHCH₃), 1.44 (s, 9H, t-Bu), 2.35 (s, 3H, C(O)CH₃), 3.02 (d, J=6 Hz, 2H, CHCH₂), 3.59–4.02 (m, 1H, CHCH₂), 4.73 (br d, J=8 Hz, 1H, NH). Anal. Calcd. for C₁₀H₁₉NO₃S: C, 51.48; H, 8.21; N, 6.00. Found: C, 51.46; H, 8.30; N, 5.90.

(S)-1-thio-S-acetyl-2-amino-N-(tert.-butyloxycarbonyl)-3-methyl-butane (7b)

This compound was prepared in 46% yield (based on the alcohol 5b) from compound 6b (3.0 g, 8.25 mmol) as described for the synthesis of compound 7c. TLC $R_f$ 0.40 (eluent diisopropyl ether/hexane, 1/1). ¹H NMR (CDCl₃) δ 0.92 and 0.98 (dd, J=2 Hz, 6H, CH₃CHCH₃), 1.45 (s, 9H, t-Bu), 1.52–1.98 (m, 1H, CH₃CHCH₃), 2.36 (s, 3H, C(O)CH₃), 2.79–3.14 (AB part of ABX spectrum, 5 lines, 2H, CH₂S), 3.32–3.78 (m, 1H, CHCH₂), 4.25–4.64 (m, 1H, NH). CI MS, m/e 262 (M⁺+1). Anal. Calcd. for C₁₂H₂₃NO₃S: C, 55.14; H, 8.87; N, 5.36. Found: C, 55.41; H, 8.97; N, 5.36.

(S)-1-thio-S-acetyl-2-amino-N-(tert.-butyloxycarbonyl)-3-methyl-pentane (7c)

Following the same procedure as used for the preparation of compound 7a, this compound was prepared in 54% yield (based on the alcohol 5c) from compound 6c (7.0 g, 18.9 mmol). TLC $R_f$ 0.46 (eluent diisopropyl ether/hexane, 1/1). ¹H NMR (CDCl₃) δ 0.78–1.02 (m, 7H, CH₂CH₃, CHCH₃), 1.02–1.34 (m, 2H, CH₂CH₃), 1.43 (s, 9H, t-Bu), 2.35 (s, 3H, C(O)CH₃), 2.19 and 3.09 (AB part of ABX spectrum, 8 lines, $J_{AX}$=1.5 Hz, $J_{BX}$=6.5 Hz, $J_{AB}$=14 Hz, 2H, CH₂S), 3.36–3.84 (m, 1H, CHCH₂S), 4.28–4.72 (m, 1H, NH). CI MS, m/e 276 (M⁺+1). Anal. Calcd. for C₁₃H₂₅NO₃S: C, 56.69; H, 9.15; N, 5.09. Found: C, 56.74; H, 9.17; N, 5.20.

(S)-1-thio-S-acetyl-2-amino-M-(tert.-butyloxycarbonyl)-3-phenyl-propane (7d)

Following the same procedure as used for the preparation of compound 7a, this compound was prepared in 66% yield (based on the alcohol 5d) from compound 6d (8.0 g, 20 mmol). TLC $R_f$ 0.35 (eluent diisopropyl ether/hexane, 1/1). ¹H NMR (CDCl₃) δ 1.41 (s, 9H, t-Bu), 2.36 (s, 3H, C(O)CH₃), 2.62–3.21 (2x AB part of ABX spectrum, 12 lines, 4H, CH₂Ph, Ch₂S), 3.73–4.20 (m, 1H, CHCH₂S), 4.37–4.76 (m, 1H, NH), 7.07–7.40 (m, 5H, Ph-H). CI MS, m/e 310 (M⁺+1). Anal. Calcd. for C₁₆H₂₃NO₃S: C, 62.11; H, 7.49; N, 4.53. Found: C, 61.93; H, 7.51; N, 4.50.

Thioacetate of N-(tert.-butyloxycarbonyl)-L-prolinol (7g)

This compound was prepared in 50% yield (based on the alcohol 5g) from compound 6g (10.3 g, 29 mmol) as described for the synthesis of compound 7a. TLC $R_f$ 0.56 (eluent diisopropyl ether/hexane, 1/1). ¹H NMR (CDCl₃) δ 1.47 (s, 9H, t-Bu, 1.57–2.10 (m, 4H, CH₂CH₂CH), 2.33 (s, 3H, C(O)CH₃), 2.84–3.53 (m, 4H, CH₂S, CH₂N), 3.73–4.09 (m, 1H, CHCH₂). CI MS, m/e 260 (M⁺+1).

($S_cR_s$) and ($S_cS_s$)-1-(chloromethyl)sulfinyl-2-(tert.-butyloxycarbonyl)amino-propane (8a and 9a)

These compounds were prepared with some modifications of the procedure described earlier[1]. Thioester 7a (14.0 g, 60 mmol) and acetic anhydride (6.12 g, 60 mmol) were dissolved in 150 mL of dry dichloromethane. The solution was stirred and cooled to −10° C. Subsequently, a solution of 8.9 g of dry gaseous chlorine (the theoretically necessary amount of chlorine was 120 mmol, 8.4 g) in 20 mL of dry dichloromethane—cooled at −50° C.—was added via a connecting tube. The temperature of the reaction mixture was kept below 0° C. After the addition had been completed, the cooling was removed and the reaction mixture was allowed to warm and was stirred for 1 h at room temperature. The so-prepared sulfinyl chloride precipitated. Subsequently, 200 mL of dry carbon tetrachloride was added and the organic solvents were evaporated in vacuo at room temperature. The residue was stripped with another 200 mL of dry carbon tetrachloride to remove the acetyl chloride.

The thus-isolated sulfinyl chloride was dissolved in 150 mL of dry dichloromethane and added dropwise over a period of 3 hrs to a stirred, cooled and dried (KOH pellets) solution of excess diazomethane and ether. During the reaction the remperature was kept at 0° C. The reaction mixture was stirred overnight at room temperature. The solvents were evaporated in vacuo and the crude product was purified by column chromatography on silicagel (eluent MeOH/CH$_2$Cl$_2$, gradient from 0% to 2% of MeOH) to give the diastereomeric α-chloro sulfoxides 8a and 9a in 41% overall yield. Diastereomer 9a was formed in slight excess as was determined from the $^1$H NMR spectrum of the reaction product. Separation of the diastereomeric α-chloro sulfoxides, a tedious task, was achieved by crystallization from ethyl acetate to yield pure 8a, and subsequent column chromatography on silicagel (eluent diisopropyl ether/methanol, 93/7) to yield pure 9a next to a considerable amount of a mixture of 8a and 9a. This procedure was carried out repeatedly.

For 8a: mp 177°–178° C.; TLC R$_f$ 0.23 (eluent diisopropyl ether/MeOH, 93/7). $^1$H NMR (CDCl$_3$) δ 1.42 (d, J=5 Hz, 3H, CHCH$_3$), 1.44 (s, 9H, t-Bu), 3.00 and 3.17 (AB part of ABX spectrum, 7 lines, J$_{AX}$=9.0 Hz, J$_{BX}$=5.4 Hz, J$_{AB}$=13.5 Hz, 2H, CHCH$_2$S(O)), 3.69–4.35 (m, 1H, CHCH$_3$), 4.39 and 4.49 (ABq, J$_{AB}$=11 Hz, 2H, S(O)CH$_2$Cl), 5.08 (br d, 1H, NH). CI MS, m/e 256 (M$^+$+1). Anal. Calcd. for C$_9$H$_{18}$NO$_3$SCl: C, 42.27; H, 7.09; N, 5.48. Found: C, 42.30; H, 7.13; N, 5.38. CD spectrum (acetonitrile solution): at 229 nm a single negative Cotton effect was observed (Δε= −0.6).

For 9a: mp 130° C.; TLC R$_f$ 0.25 (eluent diisopropyl ether/methanol, 93/7). $^1$H NMR (CDCl$_3$) δ 1.34 (d, J=6.6 Hz, 3H, CHCH$_3$, 1.42 (s, 9H, t-Bu), 2.89 and 3.18 (AB part of ABX spectrum, 8 lines, J$_{AX}$=9.9 Hz, J$_{BX}$=5.4 Hz, J$_{AB}$=13.5 Hz, 2H, CHCH$_2$S(O)), 3.79–4.24 (m, 1H, CHCH$_3$), 4.57 (s, 2H, (S(O)CH$_2$Cl), 4.73 (br d, 1H, NH). CI MS, m/e 256 (M$^+$+1). Anal. Calcd. for C$_9$H$_{18}$NO$_3$SCl: C, 42.27; H, 7.09; N, 5.48. Found: C, 42.04; H, 7.10; N, 5.50. CD spectrum (acetonitrile solution): at 229 nm a single positive Cotton effect was observed (Δε= +0.6).

(S$_c$R$_s$)-1-(chloromethyl)sulfinyl-2-(tert.-butyloxycarbonyl)amino-3-methyl-butane (8b)

Following the same procedure as used for the preparation of compounds 8a and 9a, this compound was prepared from compound 7b (2.3 g, 8.82 mmol). Due to the small difference in the R$_f$-values of the diastereomeric α-chloro sulfoxides 8b and 9b only 120 mg (8%) pure 8b could be isolated by combined silicagel column chromatography and crystallization from ethyl acetate mp: 180°–181° C. TLC R$_f$ 0.32 (eluent MeOH/CHCl$_3$, 3/97). $^1$H NMR (CDCl$_3$) δ 0.99 (d, J=7 Hz, 6H, CH$_3$CHCH$_3$), 1.44 (s, 9H, t-Bu), 1.88–2.14 (m, 1H, CH$_3$CHCH$_3$), 2.84–3.39 (AB part of ABX spectrum, m, 2H, CHCH$_2$), 3.62–4.00 (m, 1H, CHCH$_2$), 4.44 and 4.48 (ABq, J$_{AB}$=11 Hz, 2H, S(O)CH$_2$Cl), 4.76–5.09 (m, 1H, NH). CI MS, m/e 284 (M$^+$+1). Anal. Calcd. for C$_{11}$H$_{22}$NO$_3$SCl: C, 46.55; H, 7.81; N, 4.94. Found: C, 46.52; H, 7.75; N, 4.76.

(S$_c$R$_s$)-1-(chloromethyl)sulfinyl-2-(tert.-butyloxycarbonyl)-amino-3-methyl-pentane (8c)

This compound was prepared in 16% overall yield from compound 7c (2.8 g, 10 mmol) as described for the synthesis of compounds 8a and 8b. Due to the small difference in R$_f$-values of the diastereomeric α-chloro sulfoxides 8c and 9c only 236 mg (16%) pure 8c could be isolated by column chromatography using silicagel and subsequent crystallization from ethyl acetate. TLC R$_f$ 0.28 (eluent MeOH/CHCl$_3$, 3/97). $^1$H NMR (CDCl$_3$) δ 0.74–1.05 (m, 6H, CH$_2$CH$_3$, CHCH$_3$), 1.10–1.53 (m, 3H, CH$_2$CH$_3$, CHCH$_3$), 1.45 (s, 9H, t-Bu), 2.81–3.24 (AB part of ABX spectrum, m, 2H, CHCH$_2$S(O)), 3.77–4.05 (m, 1H, CHCH$_2$S(O)), 4.44 and 4.52 (ABq, J$_{AB}$=11 Hz, 2H, S(O)CH$_2$Cl), 4.80–5.14 (br d, 1H, NH).

(S$_c$R$_s$)-1-(chloromethyl)sulfinyl-2-(tert.-butoxycarbonyl)amino-3-phenyl-propane (8d)

Following the same procedure as used for the preparation of compounds 8a and 9a, this compound was prepared in 15% overall yield from compound 7d (4.0 g, 12.9 mmol). Due to the small difference in R$_f$-values of the diastereomeric α-chloro sulfoxides 8d and 9d only 320 mg (15%) pure 8d could be isolated by combined column chromatography using silicagel and subsequent crystallization from ethyl acetate: mp 144°–146° C. TLC R$_f$ 0.30 (eluent MeOH/CHCl$_3$, 3/97). $^1$H NMR (CDCl$_3$) δ 1.42 (s, 9H, t-Bu), 1.92–2.85 (m, 4H, CH$_2$Ph, CHCH$_2$S(O)), 4.05–4.37 (m, 1H, CHCH$_2$), 4.35 and 4.49 (ABq, J$_{AB}$=11 Hz, 2H, S(O)CH$_2$Cl), 5.28–5.36 (m, 1H, NH), 7.25 (br s, 5H, Ph-H). CI MS, m/e 332 (M$^+$+1). Anal. Calcd. for C$_{15}$H$_{22}$NO$_3$SCl: C, 54.29; H, 6.68; N, 4.22. Found: C, 54.39; H, 6.69; N, 4.21.

(S$_c$R$_s$)/(S$_c$S$_s$)-1(tert.-butyloxycarbonyl)-2-(chloromethylsulfinylmethyl)pyrrolidine (8g/9g)

Following the same procedure as used for the preparation of compounds 8a and 9a, this compound was prepared in 40% overall yield as a mixture of diastereomers from compound 7g (3.3 g, 12.7 mmol). (Unfortunately, attempts to separate the diastereomers failed. TLC R$_f$ 0.35 (eluent MeOH/CHCl$_3$, 3/97). $^1$H NMR (CDCl$_3$) δ 1.46 (s, 9H, t-Bu), 1.71–2.33 (m, 4H, CH$_2$CH$_2$CH), 2.74 and 2.84 (part of AB part of ABX spectrum, 4 lines, J$_{AB}$=13 Hz, J$_{AX}$ or J$_{BX}$=9 Hz, CHCH$_2$S(O)), 3.02–3.62 (m, CH$_2$N, CHCH$_2$S(O)), 4.02–4.38 (m, 1H, CHCH$_2$), 4.38–4.87 (m, 2H, S(O)CH$_2$Cl). CI MS, exact mass calcd. for C$_{11}$H$_{21}$NO$_3$SCl, m/e 282.0931 (M$^+$+1). Found: 282.0921.

(S$_c$R$_s$) and (S$_c$S$_s$)-1-(methylthiomethyl)sulfinyl-2-(tert.-butoxycarbonyl)amino-propane (10a and 11a)

Following the same procedure as described earlier1,2, the α-chloro sulfoxides 8a (3.6 mmol) and 9a (2.0 mmol) were allowed to react with sodium methyl mercaptide in ethanol to give the desired compounds 10a and 11a in 98% and 92% yield, respectively.

For 10a: TLC R$_f$ 0.18 (eluent ethyl acetate/hexane, 3/1). $^1$H NMR (CDCl$_3$) δ 1.42 (d, J=6 Hz, 3H, CHCH$_3$), 1.44 (s, 9H, t-Bu), 2.33 (s, 3H, SCH$_3$), 2.85 and 3.13 (AB part of ABX spectrum, 8 lines, J$_{AX}$=8.1 Hz, J$_{BX}$=4.5 Hz, J$_{AB}$=13.5 Hz, 2H, CHCH$_2$S(O)), 3.69 and 3.75 (ABq, J$_{AB}$=13.5 Hz, 2H, S(O)CH$_2$S), 3.97–4.48 (m, 1H, CHCH$_3$), 4.97–5.40 (m, 1H, NH). EI MS, m/e 268 (M$^+$+1). Anal. Calcd. for C$_{10}$H$_{21}$NO$_3$S$_2$: C, 44.92; H, 7.92; N, 5.24. Found: C, 45.77; H, 8.04; N, 5.25.

For 11a: TLC R$_f$ 0.18 (eluent ethyl acetate/hexane, 3/1). $^1$H NMR (CDCl$_3$) δ 1.37 (d, J=6.9 Hz, 3H, CHCH$_3$), 1.44 (s, 9H, t-Bu), 2.33 (s, 3H, SCH$_3$), 2.89 and 3.16 (AB part of ABX spectrum, 8 lines, J$_{AX}$=7.2 Hz, J$_{BX}$=5.4 Hz, J$_{AB}$=13.5 Hz, 2H, CHCH$_2$S(O)), 3.72 and 3.88 (ABq, J$_{AB}$=13.5 Hz, 2H, S(O)CH$_2$S), 3.88–4.33 (m, 1H, CHCH$_3$), 5.02 (br d, J=8 Hz, 1H, NH). EI MS, m/e 268 (M$^+$+1).

($S_cR_s$)-1-(methylthiomethyl)sulfinyl-2-(tert.-butyloxycarbonyl)amino-3-methyl-butane (10b)

This compound was prepared in 88% yield from the α-chloro sulfoxide 8b (120 mg, 0.42 mmol) by treatment with sodium methyl mercaptide following the same procedure that has been decribed earlier[1,2], TLC $R_f$ 0.21 (eluent MeOH/diisopropyl ether, 7/93). $^1$H NMR (CDCl$_3$) δ 0.96 (d, J=6.4 Hz, 6H, CH$_3$CHCH$_3$), 1.41 (s, 9H, t-Bu), 1.81–2.23 (m, 1H, CH$_3$CHCH$_3$), 2.30 (s, 3H, SCH$_3$), 2.84 and 3.15 (AB part of ABX spectrum, 8 lines, $J_{AX}$=8.3 Hz, $J_{BX}$=3.2 Hz, $J_{AB}$=12.9 Hz, 2H, CHCH$_2$S(O)), 3.60–4.08 (m, 1H, CHCH$_2$), 3.68 and 3.74 (ABq, $J_{AB}$=13.6 Hz, 2H, S(O)CH$_2$S), 5.08 (br d, J=9 Hz, 1H, NH). CI MS, exact mass calcd. for C$_{12}$H$_{26}$NO$_3$S$_2$, m/e 296.1354 (M$^+$+1). Found: 296.1358. Anal. Calcd. for C$_{12}$H$_{25}$NO$_3$S$_2$: C, 48.78; H, 8.53: N, 4.74 Found: C, 48.85; H, 8.90; N, 4.75.

($S_cR_s$)-1-(methylthiomethyl)sulfinyl-2-(tert.-butoxycarbonyl)amino-3-methyl-pentane (10c)

Following the same procedure as described earlier[1,2], the α-chloro sulfoxide 8c (236 mg, 0.79 mmol) was allowed to react with sodium methyl mercaptide in ethanol to give the desired compound 10c in 92% yield. TLC $R_f$ 0.65 (eluent MeOH/CHCl$_3$, 20/80). $^1$H NMR (CDCl$_3$) δ 0.82–1.09 (m, 6H, CHCH$_3$, CH$_2$CH$_3$), 1.09–1.95 (m, 3H, CHCH$_3$, CH$_2$CH$_3$), 1.44 (s, 9H, t-Bu), 2.32 (s, 3H, SCH$_3$), 2.74–3.38 (AB part of ABX spectrum, m, 2H, CHCH$_2$S(O)), 3.74 (s, 2H, S(O)CH$_2$Cl), 3.83–4.18 (m, 1H, CHCH$_2$S(O)), 4.94–5.27 (m, 1H, NH). Anal. Calcd. for C$_{13}$H$_{27}$NO$_3$S$_2$: C, 50.45; H, 8.79; N, 4.53. Found: C, 49.81; H, 8.83; N, 4.41. CI MS, exact mass calcd, for C$_{13}$H$_{28}$NO$_3$S$_2$, m/e 310.1511 (M$^{30}$+1). Found: 310.1503.

($S_cR_s$)-1-(methylthiomethyl)sulfinyl-2-(tert.-butyloxycarbonyl)amino-3-phenyl-propane (10d)

Following the same procedure as described earlier[1,2], the α-chloro sulfoxide 8d (310 mg, 0.94 mmol) was allowed to react with sodium methyl mercaptide in ethanol to give the desired compound 10d in 76% yield. TLC $R_f$ 0.26 (eluent ethyl acetate/hexane, 3/1). $^1$H NMR (CDCl$_3$) δ 1.42 (s, 9H, t-Bu), 2.31 (s, 3H, SCH$_3$), 2.74–3.26 (m, 4H, CHCH$_2$S(O), CH$_2$Ph), 3.71 (s, 2H, S(O)CH$_2$S), 4.04–4.43 (m, 1H, CHCH$_2$), 5.17–5.44 (m, 1H, NH), 7.24 (s, 5H, Ph-H). CI MS, m/e 344 (M$^+$+1). Anal. Calcd. for C$_{16}$H$_{25}$NO$_3$S$_2$.½H$_2$O: C, 54.52 H, 7.15; N, 3.97. Found: C, 54.61; H, 7.33; N, 3.82.

($S_cR_s$)-1-(n-butylthiomethyl)sulfinyl-2-(tert.-butyloxycarbon)amino-propane (10e)

This compound was prepared in 95% yield from the α-chloro sulfoxide 8a (1.17 g, 4.6 mmol) by treatment with sodium butyl mercaptide which was prepared in situ by reaction of sodium (4.6 mmol) with freshly distilled 1-butanethiol (5.0 mmol) in 20 mL of ethanol. The reaction mixture was worked up following the procedure that has been described earlier[1,2]. TLC $R_f$ 0.42 (eluent MeOH/CHCl$_3$, 3/97). $^1$H NMR (CDCl$_3$) δ 0.93 (t, J=6 Hz, 3H, CH$_2$CH$_3$), 1.23–1.80 (m, 4H, CH$_2$CH$_2$CH$_3$), 1.41 (D, J=6 Hz, 3H, CHCH$_3$), 1.44 (s, 9H, t-Bu), 2.74 (t, J=7 Hz, 2H, SCH$_2$CH$_2$), 2.82 and 3.20 (AB part of ABX spectrum, 8 lines, $J_{AX}$=7.0 Hz, $J_{BX}$=4.4 Hz, $J_{AB}$=13.0 Hz, 2H, CHCH$_2$S(O)), 3.76 (s, 2H, S(O)CH$_2$S), 4.02–4.43 (m, 1H, CHCH$_2$), 5.06–5.41 (m, 1H, NH). CI MS, exact mass calcd. for C$_{13}$H$_{28}$NO$_3$S$_2$, m/e 310.1511 (M$^+$+1). Found: 310.1512. Anal. Calcd. for C$_{13}$H$_{27}$NO$_3$S$_2$: C, 50.45; H, 8.79; N, 4.53. Found: C, 50.22; H, 8.76; N, 4.44.

($S_cR_s$)-1-(n-octylthiomethyl)sulfinyl-2-tert.-butyloxycarbonyl)amino-propane (10f)

This compound was prepared in quantitative yield from the α-chloro sulfoxide 8a (315 mg, 1.23 mmol) by treatment with sodium octyl mercaptide which was prepared in situ by reaction of sodium (1.35 mmol) with freshly distilled 1-octanethiol (1.48 mmol) in 10 mL of ethanol. The reaction mixture was worked up following the procedure that has been described earlier[1,2]. TLC $R_f$ 0.57 (eluent MeOH/CHCl$_3$, 20/80). $^1$H NMR (CDCl$_3$) δ 0.81 (br t, J=6 Hz, 3H, CH$_2$CH$_3$), 1.20 (br s, 13H, (CH$_2$)$_5$CH$_3$, CHCH$_3$), 1.29 (s, part of d, CHCH$_3$), 1.37 (s, 9H, t-Bu), 1.40–1.78 (m, 2H, SCH$_3$CH$_2$), 2.66 (t, J=7.2 Hz), 2H, SCH$_2$CH$_2$), 2.71 and 3.09 (AB part of ABX spectrum, 8 lines, $J_{AX}$=7.2 Hz, $J_{BX}$=5.4 Hz, $J_{AB}$=12.9 Hz, 2H, CHCH$_2$S(O)), 3.68 (s, 2H, S(O)CH$_2$S), 3.91–4.31 (m, 1H, CHCH$_3$), 5.31 (br d, J=7 Hz, 1H, NH). Anal. Calcd. for C$_{17}$H$_{35}$NO$_3$S$_2$.½H$_2$O: C, 54.51 H, 9.42; N, 3.74. Found: C, 54.23; H, 9,28; N, 3.36.

($S_cR_s$) and ($S_cS_s$)-1-(tert.-butoxycarbonyl)-2-(methylthiomethylsulfinylmethyl)pyrrolidine (10g and 11g)

These compounds were obtained in 88% yield as a mixture of diastereomers from the α-chloro sulfoxide 8g (590 mg, 2.1 mmol) by treatment with sodium methyl mercaptide in ethanol following the procedure that has been described earlier[1,2]. By careful column chromatography using silicagel two fractions weighing 278 mg (fraction 1: 45%) and 264 mg (fraction 2: 43%), enriched in compound 10g and 11g, respectively, were obtained. The ratio of compounds 10g and 11g in both fractions is unknown.

The NMR spectra of both fractions were almost identical. TLC $R_f$ 0.51 (fraction 1) and 0.47 (fraction 2) (eluent MeOH/CHCl$_3$, 3/97). $^1$H NMR (CDCl$_3$) δ 1.41 (s, 9H, t-Bu), 1.66–2.17 (m, 4H, CH$_2$CH$_2$CH), 2.28 (s, 3H, SCH$_3$), 2.49–3.47 (m, 4H, CHCH$_2$S(O)), CH$_2$N), 3.61 and 3.72 (ABq, $J_{AB}$=13.6 Hz, 2H, S(O)CH$_2$S), 3.94–4.36 (m, 1H, CHCH$_2$). CI MS, m/e 294 (M$^+$+1).

($S_cR_s$) and ($S_cS_s$)-1-(methylthiomethyl)sulfinyl-2-amino-propane (12a and 13a)

Following the same procedure as described earlier[1,2], the Boc amino protecting group of compounds 10a (2.6 mmol) and 11a (0.63 mmol) was removed by treatment with trifluoroacetic acid at 0° C. Subsequent ion-exchange column chromatography on Amberlite IRA-410 yielded compounds 12a and 13a in 93% and 95% yield, respectively.

For 12a: TLC $R_f$ 0.22 (eluent MeOH/CHCl$_3$, 20/80). $^1$H NMR (CD$_2$Cl$_2$) δ 1.28 (d, J=6.3 Hz, 3H, CHCH$_3$), 2.31 (s, 3H, SCH$_3$), 2.81 and 2.87 (AB part of ABX spectrum, 5 lines, $J_{AX}$=8.0 Hz, $J_{BX}$=4.9 Hz, $J_{AB}$=12.8 Hz, 2H, CHCH$_2$S(O)), 3.11 (br s, 2H, NH$_2$), 3.33–3.73 (m, 1H, CHCH$_3$), 3.73 and 3.80 (ABq, $J_{AB}$=13.5 Hz, 2H, S(O)CH$_2$S).

For 13a: TLC $R_f$ 0.22 (eluent MeOH/CHCl$_3$, 20/80). $^1$H NMR (CD$_2$Cl$_2$) δ 1.28 (d, J=6.3 Hz, 3H, CHCH$_3$), 1.97 (s, 2H, NH$_2$), 2.33 (s, 3H, SCH$_3$), 2.84 and 2.93 (AB part of ABX spectrum, d, 2H, CHCH$_2$S(O)), 3.46–3.71 (m, 1H, CHCH$_3$), 3.72 and 3.84 (ABq, $J_{AB}$=13.5 Hz, 2H, S(O)CH$_2$S).

($S_c R_s$)-1-(methylthiomethyl)sulfinyl-2-amino-3-methyl butane (12b)

This compound was prepared in quantitative yield from compound 10b (110 mg, 0.37 mmol) by treatment with trifluoroacetic acid at 0° C. and subsequent ion-exchange column chromatography on Amberlite IRA-410 following the procedure that has been described earlier[1,2]. TLC $R_f$ 0.59 (eluent MeOH/CHCl$_3$, 20/80). $^1$H NMR (CDCl$_3$) δ 0.84 and 0.92 (dd, J=2.3 Hz, 6H, CH$_3$CHCH$_3$), 1.43 (br s, 2H, NH$_2$), 1.43-1.84 (m, 1H, CH$_3$CHCH$_3$), 2.26 (s, 3H, SCH$_3$), 2.68 and 2.74 (AB part of ABX spectrum, doublet, J=1.5 Hz and singlet, respectively, 2H, CHCH$_2$S(O)), 2.93-3.28 (m, 1H, CHCH$_2$), 3.59 and 3.77 (ABq, $J_{AB}$=13.5 Hz, 2H, S(O)CH$_2$S).

($S_c R_s$)-1-(methylthiomethyl)sulfinyl-2-amino-3-methyl-pentane (12c)

Following the same procedure as described earlier[1,2], the Boc amino protecting group of compound 10c (207 mg, 0.67 mmol) was removed by treatment with trifluoroacetic acid at 0° C. and subsequent ion-exchange column chromatography on Amberlite IRA-410 to yield compound 12c quantitatively. $^1$NMR (CDCl$_3$) δ 0.81-1.10 (m, 6H, CHCH$_3$, CH$_2$CH$_3$), 1.10-1.72 (m, 3H, CHCH$_3$, CH$_2$CH$_3$), 1.48 (br s, 2H, NH$_2$), 2.33 (s, 3H, SCH$_3$), 2.73 and 2.82 (AB part of ABX spectrum, 2H, CHCH$_2$S(O)), 3.11-3.43 (m, 1H, CHCH$_2$S(O)), 3.68 and 3.86 (ABq, $J_{AB}$=13.5 Hz, 2H, S(O)CH$_2$S).

($S_c R_s$)-1-(methylthiomethyl)sulfinyl-2-amino-3-phenyl-propane (12d)

This compound was prepared in 73% yield from compound 10d (244 mg, 0.71 mmol) by treatment with trifluoroacetic acid at 0° C. and subsequent ion-exchange column chromatography on Amberlite IRA-410 following the procedure that has been described earlier[1,2]. $^1$H NMR (CDCl$_3$) δ 1.38-1.82 (br s, 2H, NH$_2$), 2.31 (s, 3H, SCH$_3$), 2.58-3.19 (m, 4H, CH$_2$Ph, CHCH$_2$S(O)), 3.50-3.87 (m, 1H, CHCH$_2$), 3.70 (s, 2h, S(O)CH$_2$S), 7.04-7.47 (m, 5H, Ph-H).

($S_c R_s$)-1-(n-butylthiomethyl)sulfinyl-2-amino-propane (12e)

Following the same procedure as described earlier[1,2], the Boc amino protecting group of compound 10e (1.33 g, 4.3 mmol) was removed by treatment with trifluoroacetic acid at 0° C. Subsequent ion-exchange column chromatography on Amberlite IRA-410 yielded compound 12e quantitatively. TLC $R_f$ 0.61 (eluent MeOH/CHCl$_3$, 20/80). $^1$H NMR (CDCl$_3$) δ 0.92 (t, J=5.4 Hz, 3H, CH$_2$CH$_3$9, 1.28 (d, J=6.4 Hz, 3H, CHCH$_3$), 1.34-1.87 (m, 4H, (CH$_2$)$_3$CH$_3$), 2.58-3.08 (m, 4H, CHCH$_2$S(O), NH$_2$), 3.31-3.91 (m, 1H, CHCH$_3$), 3.77 (s, 2H, S(O)CH$_2$S).

($S_c R_s$)-1-(n-octylthiomethyl)sulfinyl-2-amino-propane (12f)

This compound was prepared in quantitative yield from compound 10f (434 mg, 1.23 mmol) by treatment with trifluoroacetic acid at 0° C. and subsequent ion-exchange column chromatography on Amberlite IRA-410 following the procedure that has been described earlier[1,2]. TLC $R_f$ 0.57 (eluent MeOH/CHCl$_3$, 20/80). $^1$H NMR (CD$_2$Cl$_2$) δ 0.88 (br t, J=5 Hz, 3H, CH$_2$CH$_3$), 1.28 (br s, 13H, (CH$_2$)$_5$CH$_3$, CHCH$_3$), 1.33 (s, part of d, CHCH$_3$), 1.48 -1.84 (m, 2H, SCH$_2$CH$_2$), 2.04 (s, 2H, NH$_2$), 2.56-3.31 (m, 4H, CHCH$_2$S(O), SCH$_2$CH$_2$), 3.42-3.84 (m, 1H, CHCH$_3$), 3.80 (s, 2H, S(O)CH$_2$S).

($S_c R_s$) and ($S_c S_s$)-2-(methylthiomethylsulfinylmethyl)-pyrrolidine (12g and 13g)

These compounds were prepared in 97% and 92% yield from compounds 10g (fraction 1, 278 mg, 0.95 mmol) and 11g (fraction 2, 264 mg, 0.90 mmol), respectively, by treatment with trifluoroacetic acid at 0° C. and subsequent ion-exchange column chromatography on Amberlite IRA-410 following the procedure that has been described earlier[1,2].

For fraction 1: $^1$H NMR (CDCl$_3$) δ 1.40-2.42 (m, 4H, CH$_2$CH$_2$CH), 2.23 (s, 3H, SCH$_3$), 2.61-3.48 (m, 4H, CHCH$_2$S(O), CH$_2$N), 3.48-3.92 (m, 1H, CHCH$_2$), 3.65 and 3.93 (ABq, $J_{AB}$=13.5 Hz, 2H, S(O)CH$_2$S), 6.27 (br s, 1H, NH). CI MS, m/e 194 (M+ +1).

For fraction 2: $^1$H NMR (CDCl$_3$) δ 1.43-2.08 (m, 4H, CH$_2$CH$_2$CH), 2.21 (s, 1H, NH), 2.33 (s, 3H, SCH$_3$), 2.76-3.17 (m, 4H, CHCH$_2$S(O), CH$_2$N), 3.43-3.83 (m, 1H, CHCH$_2$), 3.67 and 3.95 (ABq, $J_{AB}$=13.5 Hz, 2H, S(O)CH$_2$S).

($S_c R_s$)-1-(methylthiomethyl)sulfinyl-2-[β-(6-methyl-5-uracilyl)acrylamido]-propane (2a)

This compound was prepared by a mixed anhydride coupling procedure. To a solution of 6-methyl-uracil acrylic acid 14 (784 mg, 4.0 mmol) in 5 mL of DMF at 0° C., was added triethyl amine (404 mg, 4.0 mmol) and isobutyl chloroformate (544 mg, 4.0 mmol). After 5 min, a solution of 12a (664 mg, 4.0 mmol) in 10 mL of DMF was added. The reaction mixture was stirred in the dark at 0° C. for 16 hrs. Evaporation of the solvent and gel filtration on Fractogel TSK HW-40(F) (eluent MeOH/H$_2$O, 85/15) afforded the desired compound 2a in 71% yield (based on the α-chloro sulfoxide 8a). TLC $R_f$ 0.53 (eluent MeOH/CHCl$_3$, 20/80). $^1$H NMR (D$_2$O) δ 1.37 (d, J=6.0 Hz, 3H, CHCH$_3$), 2.26 (s, 3H, SCH$_3$), 2.37 (s, 3H, C(6)—CH$_3$), 3.11 and 3.19 (AB part of ABX spectrum, 5 lines, $J_{AX}$=5.4 Hz, $J_{BX}$=3.6 Hz, $J_{AB}$=13.5 Hz, 2H, CHCH$_2$S(O)), 3.90 and 4.06 (ABq, $J_{AB}$=13.5 Hz, 2H, S(O)CH$_2$S), 4.31-4.62 (m, 1H, CHCH$_3$), 7.00 and 7.30 (ABq, $J_{AB}$=16.0 Hz, 2H, CH=CH). FAB MS, m/e 346 (M+ +1); [α]$^{25}$D= +77° (c=0.130, MeOH/H$_2$O, 1/1), Anal. Calcd. for C$_{13}$H$_{19}$N$_3$O$_4$S$_2$: C, 45.20; H, 5.54; N, 12.16. Found: C, 45.24; H, 5.53; N, 11.84.

($S_c S_s$)-1-(methylthiomethyl)sulfinyl-2-[β-(6-methyl-5-uracilyl)acrylamido]-propane (3a)

Following the same procedure as used for the preparation of compound 2a, this compound was prepared in 39% yield (81 mg) from compound 13a. The reaction product obtained was approximately a 75:25 mixture of compounds 3a and 2a. This was determined by integration of the AB quartet signals for S(O)CH$_2$S for compounds 2a and 3a in the $^1$H NMR spectrum of the reaction product. TLC $R_f$ 0.53 (eluent MeOH/CHCl$_3$, 20/80). $^1$H NMR (D$_2$) δ 1.37 (d, J=6.6 Hz, 3H, CHCH$_3$), 2.28 (s, 3H, SCH$_3$), 2.40 (s, 3H, C(6)—CH$_3$), 3.16 and 3.23 (AB part of ABX spectrum, 8 lines, $J_{AX}$=8.1 Hz, $J_{BX}$=4.5 Hz, $J_{AB}$=13.5 Hz, 2H, CHCH$_2$S(O)), 3.96 and 4.12 (ABq, $J_{AB}$=13.5 Hz, 2H, S(O)CH$_2$S), 4.31-4.57 (m, 1H, CHCH$_3$), 7.00 and 7.30 (ABq, $J_{AB}$=16.0 Hz, 2H, CH=CH). FAB MS, m/e 346 (M+ +1); [α]$^{25}$D= +63° (c=0.10, H$_2$O). Anal. Calcd. for C$_{13}$H$_{19}$N$_3$O$_4$S$_2$.2H$_2$O: C, 40.93; H, 5.02; N, 11.02. Found: C, 40.94; H, 4.78; N, 11.18.

($S_cR_s$)-1-(methylthiomethyl)sulfinyl-2-[β-(6-methyl-5-uracilyl)acrylamido]-3-methyl-butane (2b)

Following the same procedure as used for the preparation of compound 2a, this compound was prepared in 29% yield (40 mg) from compound 12b (0.37 mmol). The reaction product obtained was approximately a 75:25 mixture of compounds 2b and 3b. This was determined by integration of the AB quartet signals for CH=CH as well as from the singlet signals for SCH₃ for compounds 2b and 3b in the ¹H NMR spectrum of the reaction product. TLC $R_f$ 0.50 (eluent MeOH/CHCl₃, 20/80). ¹H NMR (CD₃OD) δ 1.04 (d, J=6.6 Hz, 6H, CH₃CHCH₃), 1.80–2.18 (m, 1H, CH₃CHCH₃), 2.34 (for 3b: 2.37) (s, 3H, SCH₃), 2.41 (s, 3H, C(6)—CH₃), 2.39–3.22 (m, 2H, CHCH₂S(O)), 3.89 and 4.04 (ABq, $J_{AB}$=13.8 Hz, 2H, S(O)CH₂S), 4.23–4.52 (m, 1H, CHCH₂), 7.29 and 7.49 (for 3b: 7.28 and 7.48) (ABq, $J_{AB}$=15.3 Hz, 2H, CH=CH). FAB MS, m/e 374 (M⁺+1); [α]²⁵D=+92° (c=0.20, MeOH/H₂O, 1/1).

($S_cR_s$)-1-(methylthiomethyl)sulfinyl-2-[β-(6-methyl-5-uracilyl)acrylamido]-3-methyl-propane (2c)

Following the same procedure as used for the preparation of compound 2a, this compound was prepared in 20% yield (50 mg) from compound 12c (0.67 mmol). TLC $R_f$ 0.52 (eluent MeOH/CHCl₃, 20/80). ¹H NMR (CD₃OD) δ 0.79–1.09 (m, 6H, CHCH₃, CH₂CH₃), 1.09–1.91 (m, 3H, CHCH₃, CH₂CH₃), 2.32 (s, 3H, SCH₃), 2.39 (s, 3H, C(6)—CH₃), 2.76–3.24 (m, 2H, CHCH₂S(O)), 3.85 and 3.99 (ABq, $J_{AB}$=14 Hz, 2H, S(O)CH₂S), 4.28–4.61 (m, 1H, CHCH₂S(O)), 7.26 and 7.45 (ABq, $J_{AB}$=15.5 Hz, 2H, CH=CH). FAB MS, m/e 388 (M⁺+1); [α]²⁵D=+92° (c=0.064, MeOH/H₂O, 1/1). Anal. Calcd. for C₁₆H₂₅N₃O₄S₂·1½H₂O: C, 46.36; H, 6.08; N, 10.14. Found: C, 46.29; H, 5.94; N, 9.71

($S_cR_s$)-1-(methylthiomethyl)sulfinyl)-2-[β-(6-methyl-5-uracilyl)acrylamido]-3-phenyl-propane (2d)

Following the same procedure as described for the preparation of compound 2a, this compound was prepared in 51% yield (112 mg) from compound 12d (126 mg, 0.52 mmol). TLC $R_f$ 0.81 (eluent MeOH/CHCl₃, 20/80). ¹H NMR (CD₃OD) δ 2.30 (s, 3H, SCH₃), 2.37 (s, 3H, C(6)—CH₃), 2.28–3.26 (m, 4H, CHCH₂S(O), CH₂Ph), 3.83 and 3.97 (ABq, $J_{AB}$=13.7 Hz, 2H, S(O)CH₂S), 4.49–4.82 (m, 1H, CHCH₂), 7.19 and 7.41 (ABq, $J_{AB}$=15.3 Hz, 2H, CH=CH), 7.29 (s, 5H, Ph-H). FAB MS, m/e 422 (M⁺+1); [α]²⁵D=+21° (c=0.06, MeOH/H₂O, 1/1). Anal. Calcd. for C₁₉H₂₃N₃O₄S₂·½H₂O: C, 51.92; H, 5.27; N, 9.56. Found: C, 52.75; H, 5.50; N, 9.20.

($S_cR_s$)-1-(n-butylthiomethyl)sulfinyl-2-[β-(6-methyl-5-uracilyl)acrylamido]-propane (2e)

This compound was prepared in 37% yield (620 mg) from compound 12e (1.33 g, 4.30 mmol), following the same procedure as used for the preparation of compound 2a. TLC $R_f$ 0.66 (eluent MeOH/CHCl₃, 20/80). ¹H NMR (CD₃OD) δ 0.77 (br t, J=6.3 Hz, 3H, CH₂CH₃), 1.20 (d, J=6.9 Hz, 3H, CHCH₃), 1.10–1.68 (m, 4H, CH₂CH₂CH₃), 2.18 (s, 3H, C(6)—CH₃), 2.60 (t, J=7.2 Hz, 2H, SCH₂CH₂), 2.79 and 3.03 (AB part of ABX spectrum, $J_{AX}$=9.3 Hz, $J_{BX}$=4.4 Hz, $J_{AB}$=13.0 Hz, 2H, CHCH₂S(O)), 3.70 and 3.83 (ABq, $J_{AB}$=13.6 Hz, 2H, S(O)CH₂S), 4.21–4.57 (m, 1H, CHCH₃), 7.02 and 7.27 (ABq, $J_{AB}$=15.0 Hz, 2H, CH=CH). FAB MS, m/e 388 (M⁺+1); [α]²⁵D=+80° (c=0.115, MeOH/H₂O, 1/1). Anal. Calcd. for C₁₆H₂₅N₃O₄S₂·H₂O: C, 47.39; H, 6.21; N, 10.36. Found: C, 47.47; H, 6.47; N, 10.32.

($S_cR_s$)-1-(n-octylthiomethyl)sulfinyl-2-[β-(6-methyl-5-uracilyl)acrylamido]-propane (2f)

Following the same procedure as described for the preparation of compound 2a, this compound was prepared in 50% yield (272 mg) (based on the α-chloro sulfoxide 8a) from compound 12f (340 mg, 1.24 mmol). TLC $R_f$ 0.71 (eluent MeOH/CHCl₃, 20/80). ¹H NMR (CD₃OD) δ 0.91 (br t, J=5.5 Hz, 3H, CH₂CH₃), 1.28 (br s, 10H, (CH₂)₅CH₃), 1.37 (d, J=8.0 Hz, 3H, CHCH₃), 1.52–1.82 (m, 2H, SCH₂CH₂), 2.35 (s, 3H, C(6)—CH₃), 2.77 (t, J=7.0 Hz, 2H, SCH₂CH₂), 3.30 (d, J=5.0 Hz) and 3.17 (d, J=9.0 Hz, AB part of ABX spectrum, 2H, CHCH₂S(O)), 3.88 and 3.95 (ABq, $J_{AB}$=13.5 Hz, 2H, S(O)CH₂S), 4.42–4.51 (m, 1H, CHCH₃), 7.18 and 7.42 (ABq, $J_{AB}$=16.0 Hz, 2H, CH=CH). FAB MS, m/e 444 (M⁺+1); [α]²⁵D=+93° (c=0.102, MeOH). Anal. Calcd. for C₂₀H₃₃N₃O₄S₂: C, 54.15; H, 7.50; N, 9.47. Found: C, 53.92; H, 7.53; N, 9.21.

($S_cR_s$) and ($S_cS_s$)-1-[β-(6-methyl-5-uracilyl)acrylamido]-2-(methylthiomethylsulfinylmethyl)pyrrolidine (2g and 3g)

These compounds were prepared in 36% yield (123 mg) and 72% yield (209 mg) from compounds 12g (fraction 1, 178 mg, 0.92 mmol) and 13g (fraction 2, 150 mg, 0.78 mmol), respectively, following the same procedure as used for the preparation of compound 2a.

For 2g: TLC $R_f$ 0.58 (eluent MeOH/CHCl₃, 20/80). ¹H NMR (CD₃OD) δ 1.98–2.29 (m, 4H, CH₂CH₂CH), 2.38 (s, 3H, SCH₃), 2.41 (s, 3H, C(6)—CH₃), 2.98–3.56 (m, 2H, CHCH₂S(O)), 3.56–3.90 (m, 2H, CH₂N), 4.06 and 4.34 (ABq, $J_{AB}$=13.8 Hz, 2H, S(O)CH₂S), 4.47–4.77 (m, 1H, CHCH₂), 7.53 (s, 2H, CH=CH). FAB MS, m/e 372 (M⁺+1).

Biological activity

The biological activity of the present compounds has been investigated by in vitro clonogenic assay. Colony assays are much used to measure the response of known lines of animal and human tumor cells to treatment with cytotoxic agents. Recently, for example, the Raji cell culture line of Burkitt's lymphoma (J. Natl. Cancer Inst. (1982), 68, 115) has been used to determine the effect of various anticancer medicaments on the capacity of these cells to form colonies in soft agar. The results raise the assumption that known human tumor cell lines can be used for selecting novel anticancer medicaments. The growth of tumor colonies in soft agar from primary human tumor explants is still more promising (Nature (1967), 263, 771; and Science (1977), 197, 461).

Results so far show an accuracy of the analysis of 90–95% in predicting clinical resistance and of 60–65% in predicting a clinical response (N. Engl. J. Med. (1978), 298, 1321; and Lancet. (1980), 2, 340). This analysis is possibly of importance as a selection test for novel antitumor medicaments (Europ. J. Cancer (1981), 17, 129).

The in vitro clonogenic assay was effected in Leukemia L 1210 cells in soft agar medium (0.3%). There is a good correlation between the activity in vitro and that in vivo of the medicaments investigated. On the basis of the findings in the in vitro analysis, therefore, the in vivo activity can be predicted with good results. In the analysis, the inhibition of the L 1210 colony formation by sparsomycin and derivatives thereof is determined for various concentrations, and the dose giving 50% inhibition of the colony formation, as compared with non-treated control cells is calculated ($ID_{50}$). The analysis is carried out as follows (variant of the method described in Cancer Chemother. Rep. (1967), 51, 451).

From a suspension culture one hundred L 1210 cells are plated out in 35 mm culture dishes (Falcon) containing 1 ml soft agar culture medium and the compound to be investigated in suitable concentrations. The soft agar culture medium consists of Dulbecco's medium supplemented with 20% horse serum, 60 μmole 2-mercaptoethanol, 20 mg/ml L-asparagine, 75 mg/ml DEAE dextran (molecular weight $2 \times 10^6$) and 0.3% bacto agar (Difco). The culture dishes were incubated at 37° C. in an atmosphere of 10% $CO_2$ in humidified air for 3 days. After this period of continuous exposure to the medicament the colonies were counted and dose-effect curves made. From these curves, the medicament dose is calculated which causes 50% inhibition of the colony formation as compared with non-treated control cells.

The results are summarized in the following Table 1. It appears therefrom that the inhibition of L 1210 colony formation by compounds (2a) and (2f) is of the same level as obtained with n-octylsparsomycin and benzylsparsomycin. The low activity for compound (3a) proves that the chirality at the S atom of the sulfoxide group is important for the antitumor activity.

TABLE 1

| $L_{1210}$ clonogenic assay | |
|---|---|
| | $ID_{50}$ (μM) |
| (1) Sparsomycin | 0.40 |
| n-octyl-sparsomycin | 0.10 |
| benzyl-sparsomycin | 0.11 |
| (2a) Ala—sparsomycin | 0.10 |
| (3a) S—epimer Ala-sparsomycin | 0.55 |
| (2f) ηn-octyl-Ala—sparsomycin | 0.18 |

The activity of the novel compounds was also measured in two cell-free systems, namely *Saccharomyces cerevisiae* and *E. coli*, a prokaryotic and a eukaryotic system, respectively.

The peptidyl transferase activity was measured by the polyphenylalanine synthesis assay (Nirenberg and Matthei, Proc. Natl. Acad. Sci. USA 47 (1961) 1588), the fragment reaction (Monro, Methods Enzymol. 20 (1971) 472) and the puromycin reaction. In all the in vitro tests, i.e. polyPhe synthesis, fragment reaction and puromycin reaction, ribosomes from *E. coli* MRE600 and *S. cerevisiae* Y166 were used. The reaction mixture for polyphenylalanine synthesis was slightly different for *E. coli* and *S. cerevisiae*.

*E. coli*: The reaction mixture (50 μl) contained 50 mM Tris-HCl pH 7.6, 15 mM $MgCl_2$, 90 mM KCl, 15 mM β-mercapto ethanol, 1 mM GTP, 10 mM ATP, 0.2 mg/ml of polyuridylic acid, 1.5 mg/ml tRNA, 0.3 μM of ribosomes, 2.5 mg/ml of phosphoenol pyruvate, 20 μg/ml of pyruvate kinase, the required concentration of sparsomycin or its analogue and 5 μl of supernatant fraction S-100. Subsequently, [$^3$H]phenylalanine, 30 μM (about 60 cpm/pmol) was added to start the reaction. Incubation was at 37° C. for 30 min. The reaction was stopped by the addition of 1 ml of 10% TCA and the samples were filtered through glass fiber filters. The filters were washed with 10 ml of cold 10% TCA, dried and counted for radioactivity.

*S. cerevisiae*: The test was carried out as indicated above for *E. coli*. The phosphoenol pyruvate and pyruvate kinase were, however, replaced by creatine phosphate (20 mM) and creatine phosphokinase (50 μg/ml). The incubation was performed at 30° C. for 30 min and the samples were processed as described above. Under these conditions the control samples polymerized 5–14 and 3–8 molecules of phenylalanine per ribosome derived from *E. coli* and *S. cerevisiae*, respectively. Ribosomes and supernatant factors from *E. coli* and *S. cerevisiae* were prepared according to standard procedures, described by Staehelin and Maglott, Methods Enzymol. 20 (1971) 449, and by Sanchez-Madrid et al, Eur. J. Biochem. 98 (1979) 409.

The fragment reaction was carried out in 150 μl of 33 mM Tris-HCl pH 7.4, 270 mM KCl, 13 mM magnesium acetate containing 1 mg/ml of ribosomes, 2 mM puromycin, 1 pmol of N-acetyl-[$^3$H]Leu-ACCAC(U), the required concentration of sparsomycin or its analogue and 33% methanol. The reaction was initiated by the addition of the alcohol and allowed to proceed at 0° C. for 30 min, and was then stopped by the addition of 100 μl of 0.3M sodium acetate pH 5.5 saturated with $MgSO_4$. The samples were extracted with 1.5 ml of ethyl acetate and 1 ml of the organic phase was checked for radioactivity. The 3' terminal pentanucleotide N-acetyl-[$^3$H]Leu-ACCAC(U) was prepared from N-acetyl-[$^3$H]Leu-tRNA by ribonuclease T1 as described by Monro.

The puromycin reaction was carried out in 25 μl of 30 mM KCl, 50 mM $NH_4Cl$, 30 mM Tris-HCl pH 7.8, 20 mM $MgCl_2$, 10 pmol of ribosomes, 100 μg/ml of poly(U) and 15 pmol of N-acetyl-[$^3$H]Phe-tRNA. The reaction mixture was incubated for 30 min at 37° C. and then 1 μl of 20 mM puromycin was added and incubation was followed for 5 more min. To the samples 250 μl of 0.1M sodium carbonate and 0.7 ml of ethyl acetate were added, shaken for 1 min, centrifuged to separate the phases and 0.5 ml of the upper organic phase taken for estimating the radioactivity.

The results are summarized in the following table 2. The concentration of sparsomycin or an analog giving 50% inhibition of the protein synthesis relative to the control is given in $ED_{50}$.

TABLE 2

| | In vitro peptide bond formation assays: $ED_{50}$ (μM) | | | | |
|---|---|---|---|---|---|
| | polyPhe synthesis | | Fragment reaction | | Puromycin reaction |
| | E. coli | S. cerevisiae | E. coli | S. cerevisiae | E. coli |
| (1) Sparsomycin | 8.5 | 5.2 | 3.2 | 2.8 | 0.1 |
| n-octyl-sparsomycin | 1.6 | 1.3 | 60 | 300 | 0.25 |
| benzyl-sparsomycin | 0.6 | 0.6 | 7.6 | 2.6 | 0.13 |
| (2a) Ala—sparsomycin | 15.1 | 7.5 | 4.7 | 5.7 | 0.9 |
| (3a) S—epimer Ala—sparsomycin | 283 | 143 | 55 | 68 | 2.7 |

It will be apparent from the results given in table 2 that ala-sparsomycin (2a) is an effective inhibitor of protein biosynthesis, although less effective than sparsomycin itself and the n-octyl and benzyl derivatives. The relatively high activity of ala-sparsomycin and benzyl-sparsomycin in the fragment reaction, compared to the activity found with n-octylsparsomycin, reflects the lower lipophilicity of these two compounds.

Inhibition of bacterial growth was tested in solid as well as in liquid medium. For the test on agar plates, petri dishes containing 15 ml of LB medium (10 g/l bactotryptone, 5 g/l yeast extract and 5 g/l NaCl) were covered with 5 ml of the same medium—kept melted at 40° C.—containing 40 μl of a culture of the required bacterium at approximately an $A_{550}$ of 2. After solidification, 3 mm filter disks containing 4 μl of a 10 mM solution of the antibiotic in 50EtOH/DMSO were placed on the surface of the agar and the plates were incubated at 37° C. for 24 h. For the test in liquid medium, E. coli MRE600 was grown in LB medium supplemented with 0.2% of glucose to exponential phase ($A_{560}=0.1$) and distributed in 1 ml aliquots in tubes containing the required amount of antibiotic. The tubes were incubated at 37° C. for 4 h, subsequently diluted with 3 ml of 0.1% of sodium azide to stop growth and the absorption at 550 nm was measured. The absorption of the medium without addition of antibiotic was considered as 100% growth.

The results are summarized in the following table 3.

TABLE 3

| Growth inhibition E. coli MRE600 | |
|---|---|
| | $ED_{50}$ (μM) |
| (1) Sparsomycin | 11 |
| n-octyl-sparsomycin | 2.5 |
| benzyl-sparsomycin | 1 |
| (2a) Ala—sparsomycin | 5.6 |
| (3a) S—epimer Ala—sparsomycin | 44 |

From table 3 it is apparent that ala-sparsomycin is also an effective inhibitor of bacterial growth, superior to sparsomycin itself but less active than the n-octyl and benzyl derivatives.

The results obtained in the assays to determine the inhibition of protein synthesis demonstrate that the assay systems concerned have little or none predictive value for the antitumor activity (L 1210 assay system) of compounds.

The antitumor activity of the present compounds has also been investigated by in vivo assays. In the assays, mice were treated for nine days in succession, starting at 24 hours after the time of tumor implant.

The results are shown in tables 4, 5 and 6 and represent the number of tumor-bearing mice surviving after administration of optimal doses of the test compound, expressed as a treatment/control (T/C×100%) ratio. In the tables, information is provided with respect to the sex, dose, weight loss of treated animals compared to control animals, and the number of survivors in groups of 6 mice.

TABLE 4

| $L_{1210}$ leukemia: φ1DX9 ip in CDF1 mice | | | | | |
|---|---|---|---|---|---|
| | sex | dose (mg/kg) | weight loss (T − C) (g) | cures | T/C (%) |
| (1) Sparsomycin | M | 0.125 | −1.2 | 0/6 | 105 |
| | F | 0.25 | −1.1 | 0/6 | 121 |
| n-octyl-sparsomycin | M | 20.0 | −0.7 | 0/6 | 152 |
| | F | 12.0 | −1.9 | 0/6 | 153 |
| benzyl-sparsomycin | M | 4.0 | −1.8 | 0/6 | 162 |
| | F | 10.0 | −1.6 | 0/6 | 217 |
| (2a) Ala—sparsomycin | M | 1.7 | −2.0 | 2/6 | 248 |
| | F | 2.5 | −1.4 | 0/6 | 184 |
| (2e) n-butyl-Ala—sparsomycin | F | 13.3 | −0.7 | 0/6 | 161 |

TABLE 5

| $P_{388}$ leukemia: φ1DX9 ip in CDF1 mice | | | | | |
|---|---|---|---|---|---|
| | sex | dose (mg/kg) | weight loss (T − C) (g) | cures | T/C (%) |
| (1) Sparsomycin | M | 0.125 | −3.0 | 0/6 | 88 |
| n-octyl-sparsomycin | M | 22.5 | −1.7 | 0/6 | 150 |
| benzyl-sparsomycin | M | 2.0 | −2.2 | 0/6 | 133 |
| (2a) Ala—sparsomycin | F | 3.4 | −2.3 | 0/6 | 170 |
| (2e) n-butyl-Ala—sparsomycin | M | 20.0 | −3.2 | 0/6 | 146 |

TABLE 6

| RC (renal cell) carcinoma: φ1DX9 ip in CDF1 mice | | | | | |
|---|---|---|---|---|---|
| | sex | dose (mg/kg) | weight loss (T − C) (g) | cures | T/C (%) |
| (1) Sparsomycin | M | 0.125 | −1.7 | 0/6 | 100 |
| n-octyl-sparsomycin | M | 20.0 | −1.6 | 0/6 | 179 |
| benzyl-sparsomycin | M | 2.7 | −1.8 | 0/6 | 158 |
| (2a) Ala—sparsomycin | M | 1.1 | −0.6 | 0/6 | 304 |
| | F | 2.3 | −1.5 | 0/6 | 300 |

It appears that ala-sparsomycin results in all different tumor models used in very high T/C-values, in particular in the L 1210 leukemia and RC-carcinoma tests.

Toxicity

The acute $LD_{50}$ values (lethal dose for 50% of the animals) are given in the following table 7. It appears therefrom that ala-sparsomycin is about 9× less toxic than sparsomycin.

TABLE 7

| Toxicity: φ1DX9 | | |
|---|---|---|
| | LD 50 in mg/kg/inj i.p. in mice | (95% confidence interval) |
| (1) Sparsomycin | 0.26 | (0.17–0.38) |
| n-octyl-sparsomycin | 29.5 | (23.7–36.7) |

TABLE 7-continued

| Toxicity: φ1DX9 | |
|---|---|
| | LD 50 in mg/kg/inj i.p. in mice (95% confidence interval) |
| benzyl-sparsomycin | 5.0 (4.0–6.3) |
| (2a) Ala—sparsomycin | 2.33 (1.83–3.16) |
| (2e) n-butyl-Ala—sparsomycin | >16 |

What I claim:

1. A sparsomycin ($S_c$-$R_s$) compound having the formula:

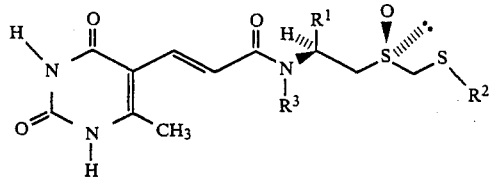

wherein $R^1$ is $C_1$-$C_6$ alkyl, benzyl, imidazolmethyl, or 3-indolylmethyl; $R^2$ is $C_1$-$C_{10}$ alkyl, or benzyl; and $R^3$ is hydrogen; or $R^1$ and $R^3$ taken together is $(CH_2)_n$ wherein n is 1, 2, 3, 4, or 5.

2. The compound according to claim 1, wherein $R_1$ is methyl, isopropyl, sec-butyl, ethyl, n-propyl, n-butyl, imidazolmethyl, 3-indolylmethyl, or benzyl, $R_2$ is methyl, ethyl, n-propyl, isopropyl, n-butyl, sec-butyl, n-pentyl, n-hexyl, n-heptyl, n-octyl or benzyl; and $R_3$ is hydrogen or $R_1$ and $R_3$ taken together is $(CH_2)_n$ wherein n is 1, 2, 3, 4, or 5.

3. The compound according to claim 1, wherein $R^1$ is methyl, $R^2$ is methyl and $R^3$ is hydrogen.

4. The compound according to claim 1, wherein $R^1$ is isopropyl, $R^2$ is methyl and $R^3$ is hydrogen.

5. The compound according to claim 1, wherein $R^1$ is sec-butyl, $R^2$ is methyl and $R^3$ is hydrogen.

6. The compound according to claim 1, wherein $R^1$ is benzyl, $R^2$ is methyl and $R^3$ is hydrogen.

7. The compound according to claim 1, wherein $R^1$ is methyl, $R^2$ is n-octyl, and $R^3$ is hydrogen.

8. The compound according to claim 1, wherein $R^1$ is methyl, $R^2$ is n-butyl and $R^3$ is hydrogen.

9. The compound according to claim 1, which has the formula:

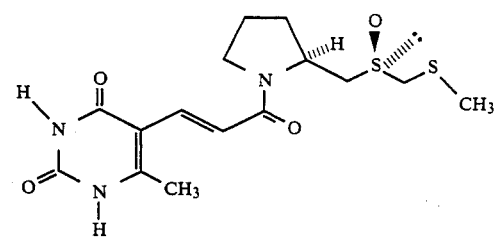

10. A pharmaceutical composition for the treatment of tumors comprising an anti-tumor effective amount of a sparsomycin ($S_c$-$R_s$) compound according to claim 1 in association with a pharmaceutically acceptable carrier, diluent, solvent or excipient.

* * * * *

UNITED STATES PATENT AND TRADEMARK OFFICE
CERTIFICATE OF CORRECTION

PATENT NO. : 4,820,712

DATED : April 11, 1989

INVENTOR(S) : Henricus C. J. Ottenheijm

It is certified that error appears in the above-identified patent and that said Letters Patent is hereby corrected as shown below:

Column 1, line 9: "pharmaceological" should read as --pharmacological--

Column 1, line 22: "543289" should read as --54328q--

Column 1, line 39: "40, 1 S63" should read as --40, S63--

Column 1, line 54: "(Biochem." should read as --(Biochim.--

Column 2, line 37: "$C_1-C_{20}$" should read as --$C_2-C_{20}$--

Column 3, line 20: "cycloalkylmethy" should read as --cycloalkylmethyl--

Column 8, line 20: "uncorrecred, $^1H$" should read as --uncorrected. $^1H$--

UNITED STATES PATENT AND TRADEMARK OFFICE
CERTIFICATE OF CORRECTION

PATENT NO. : 4,820,712

DATED : April 11, 1989

INVENTOR(S) : Henricus C. J. Ottenheijm

It is certified that error appears in the above-identified patent and that said Letters Patent is hereby corrected as shown below:

Column 8, line 57: "$CH_3CHCHC_3$" should read as --$CH_3CHCH_3$--

Column 9, line 37: "C, 54.84" should read as --C, 54.83-- (second occurrence)

Column 11, line 53: "3.59-4.02" should read as --3.59-4.03--

Column 11, line 62: "7c" should read as --7a--
Column 13, line 1: "and" should read --in--
Column 13, line 2: "remperature" should read as --temperature--

Column 15, line 34: "($M^{30}$+1)" should read as --($M^{+}$+1)--

Column 15, lines 51-52: "butyloxycarbon" should read as --butyloxycarbonyl--

Column 17, line 53: "$CH_2CH_39$," should read as --$CH_2CH_3$),--

UNITED STATES PATENT AND TRADEMARK OFFICE
CERTIFICATE OF CORRECTION

PATENT NO. : 4,820,712

DATED : April 11, 1989

INVENTOR(S) : Henricus C. J. Ottenheijm

It is certified that error appears in the above-identified patent and that said Letters Patent is hereby corrected as shown below:

Column 19, line 24: "propane" should read as --pentane--

Column 21, line 39: "ηn-octyl" should read as --n-octyl--

Signed and Sealed this

Twentieth Day of March, 1990

*Attest:*

JEFFREY M. SAMUELS

*Attesting Officer*     *Acting Commissioner of Patents and Trademarks*